(12) United States Patent
De Kort et al.

(10) Patent No.: US 9,872,888 B2
(45) Date of Patent: Jan. 23, 2018

(54) USE OF A NUCLEOTIDE FOR IMPROVING THE HEAT STABILITY OF AN AQUEOUS MICELLAR CASEIN COMPOSITION

(75) Inventors: Esther Jacqueline Petra De Kort, Wageningen (NL); Marcel Minor, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 14/232,240

(22) PCT Filed: Jul. 16, 2012

(86) PCT No.: PCT/NL2012/050509
§ 371 (c)(1),
(2), (4) Date: Jan. 10, 2014

(87) PCT Pub. No.: WO2013/012324
PCT Pub. Date: Jan. 24, 2013

(65) Prior Publication Data
US 2014/0135257 A1   May 15, 2014

(30) Foreign Application Priority Data

Jul. 18, 2011   (WO) ................ PCT/NL2011/050521

(51) Int. Cl.
| | | |
|---|---|---|
| *A61K 38/17* | (2006.01) | |
| *A23L 1/305* | (2006.01) | |
| *A23L 33/00* | (2016.01) | |
| *A23L 33/13* | (2016.01) | |
| *A23L 33/19* | (2016.01) | |
| *A61K 38/00* | (2006.01) | |

(52) U.S. Cl.
CPC .......... *A61K 38/1709* (2013.01); *A23L 33/13* (2016.08); *A23L 33/19* (2016.08); *A23L 33/40* (2016.08); *A23V 2002/00* (2013.01); *A61K 38/00* (2013.01)

(58) Field of Classification Search
CPC .......... A23L 33/19; A23L 33/40; A23L 33/13; A61K 38/1709; A61K 38/00; A23V 2002/00; A23V 2250/30; A23V 2250/54246; A23V 2200/33
USPC ........................................................ 514/1.1
See application file for complete search history.

(56) References Cited

U.S. PATENT DOCUMENTS

| | | | |
|---|---|---|---|
| 4,544,559 A | 10/1985 | Gil et al. | |
| 5,700,590 A | 12/1997 | Masor et al. | |
| 8,282,965 B2 * | 10/2012 | de Kort et al. | ....... A23L 1/0534 |
| | | | 424/682 |
| 2006/0078595 A1 * | 4/2006 | Van Leeuwen et al. | ..... 424/439 |

FOREIGN PATENT DOCUMENTS

| | | | |
|---|---|---|---|
| NL | WO2009072886 | * | 7/2009 |
| NL | WO2009082203 | * | 7/2009 |
| NL | WO2009082227 | * | 7/2009 |
| WO | WO-2009/072884 A1 | | 6/2009 |

OTHER PUBLICATIONS

Ferreira et al., "The Determination and Distribution of Nucleotides in Dairy Products using HPLC and Diode Array Detection", Food Chemistry, vol. 74, Aug. 1, 2001, pp. 239-244.
International Search Report in PCT/NL2012/050509 dated Sep. 6, 2012.
Kehagias et al., "Support of Growth and Formation of D-amino Acids by Bifidobacterium Longum in Cows', Ewes', Goats' Milk and Modified Whey Powder Products", International Dairy Journal, vol. 18, No. 4, 2008, pp. 396-402.
Michaelidou A., "Factors Influencing Nutritional and Health Profile of Milk and Milk Products", Small Ruminant Research, vol. 79, No. 1, Sep. 1, 2008, pp. 42-50.
Pandya et al, "Goat and Sheep Milk Products other than Cheeses and Yoghurt", Small Ruminant Research, vol. 68, No. 1-2, Feb. 8, 2007, pp. 193-206.
Plakantara S et al., "Nucleotides and Nucleosides in Ovine and Caprine Milk during Lactation", Journal of Dairy Science, vol. 93, No. 6, Jun. 1, 2010, pp. 2330-2337.
Spagnuolo et al., "Kappa-Carrageenan Interactions in Systems Containing Casein Micelles and Polysaccharide Stabilizers", Food Hydrocolloids, vol. 19, No. 3, May 1, 2005, pp. 371-377.

* cited by examiner

*Primary Examiner* — Yih-Horng Shiao
(74) *Attorney, Agent, or Firm* — Gilberto M. Villacorta; Sunit Talapatra; Foley & Lardner LLP

(57) ABSTRACT

The invention relates to the use of one or more nucleotides for improving the heat stability of an aqueous micellar casein composition comprising 6 to 20 g per 100 ml of micellar casein, and having a pH of about 6 to 8. The invention also relates to heat-treated liquid nutritional compositions comprising 6 to 20 g, preferably 9-20 g, of protein per 100 ml of the composition and having a pH of about 6 to 8, in which all or a major part of said protein comprises micellar casein, further comprising one or more nucleotides.

23 Claims, 4 Drawing Sheets

Figure 1:
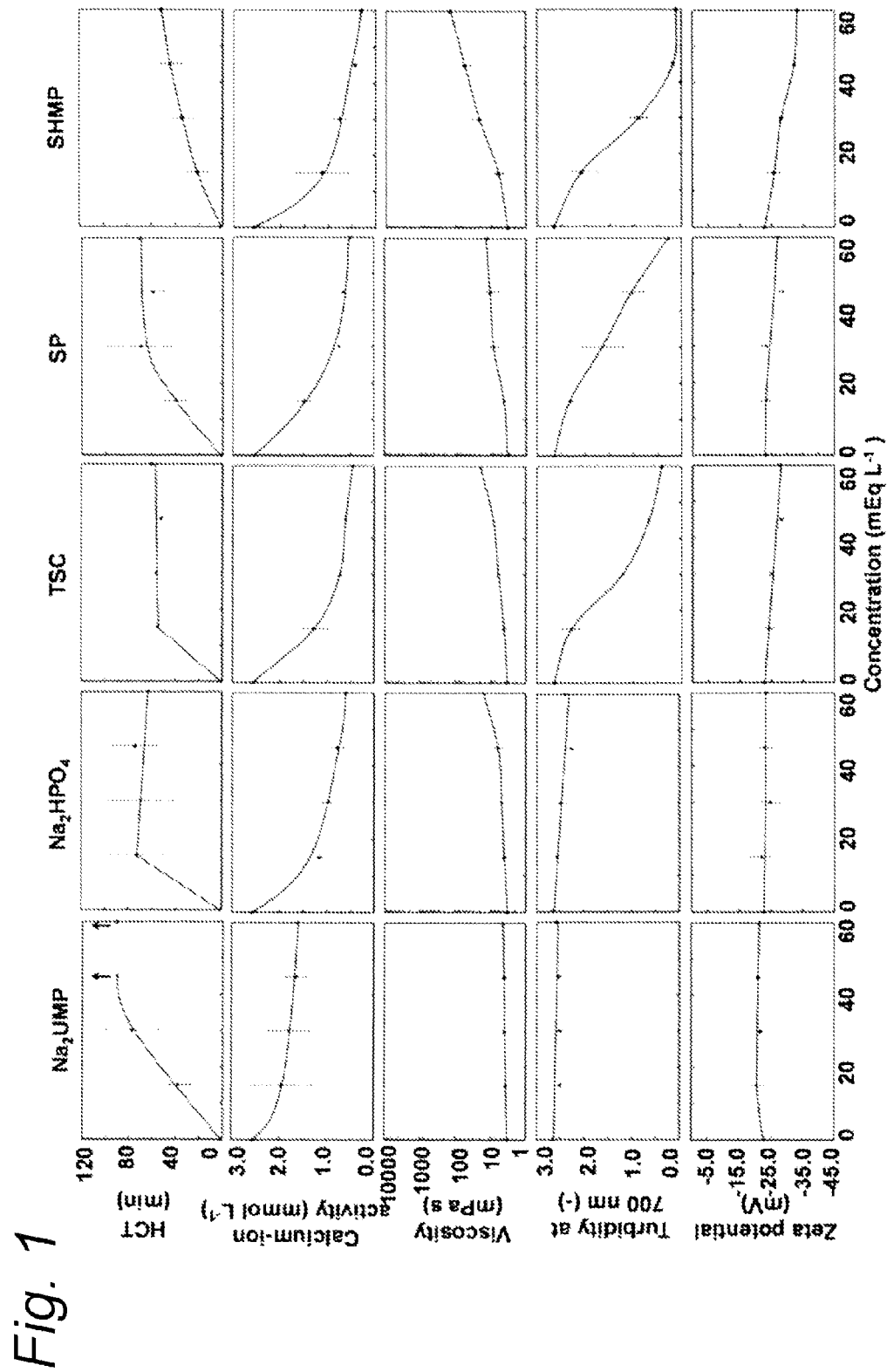

USE OF A NUCLEOTIDE FOR IMPROVING THE HEAT STABILITY OF AN AQUEOUS MICELLAR CASEIN COMPOSITION

CROSS REFERENCE TO RELATED APPLICATIONS

The present application is a National Stage of International Application No. PCT/NL2012/050509 filed on Jul. 16, 2012, which claims the benefit of international Application No: PCT/NL2011/050521 filed Jul. 18, 2011, the entire disclosures of which are incorporated herein by reference.

FIELD OF THE INVENTION

The present invention is situated in the field of enteral liquid nutritional compositions. More in particular, it relates to an aqueous micellar casein composition comprising 6 to 20 g of micellar casein per 100 ml of composition, and having a pH of about 6 to 8, as well as to an enteral liquid nutritional composition comprising a high amount of micellar casein, and to the problem of improving the heat stability during a heat treatment process, such as a sterilization or pasteurization process, of said aqueous micellar casein composition and of said enteral liquid nutritional composition comprising a high amount of micellar casein.

BACKGROUND OF THE INVENTION

Preferably, medical dairy products are highly concentrated in nutrients, in particular in proteins and minerals, to meet the daily intake of nutrients in malnourished patients. These patients can be cachectic patients or persons suffering from end-stage AIDS or cancer, or in cancer treatment, suffering from severe pulmonary diseases like COPD (chronic obstructive pulmonary disease), tuberculosis and other infection diseases, or persons that experienced severe surgery or trauma, such as burns. Furthermore, persons suffering from disorders in the throat or mouth such as oesophageal cancer or stomatitis and persons having problems with swallowing like dysphagic persons, require special liquid, low-volume concentrated liquid or semi-liquid nutrition. Also, persons just suffering from reduced appetite or loss of taste, will benefit from low-volume, preferably liquid, food. These patients can also be elderly persons, in particular frail elderly and elderly at risk of becoming frail. In this regard, although an elderly person's energy needs may be reduced, their ability to consume products may also be diminished. For example, they may have difficulty consuming a product due to, e.g., swallowing difficulties, or due to too large amount of product they need to consume to meet the daily intake of nutrients. Hence, compliance is not optimal, and often, the intake is suboptimal, leading to suboptimal nourishment, and in the end, to malnutrition. Other persons who may be interested in consuming such nutritional compositions may be healthy persons such as a sportsman or sportswoman or an active elderly, who are in need of a concentrated nutrition in a small volume, such as the low-volume liquid enteral nutritional composition according to the invention with a high content of nutrients, in particular proteins.

All aforementioned groups of patients may be extremely sensitive to food consistency and to the organoleptic properties of the product such as, for instance viscosity, mouth feel, taste, smell and colour. Also, patients such as cachectic patients, typically suffer from extreme weakness which often prevents them from sitting in a vertical position and from drinking food from a carton or even to suck it from a straw. These patients benefit well from low-volume liquid enteral nutritional compositions with a high content of nutrients, in particular proteins.

However, high amounts of protein and minerals increase the overall viscosity of the product during processing, in particular during a heat treatment such as sterilization at ultra-high temperature, so as to remain stable for at least nine months at ambient temperature, or pasteurization, and storage because of shifts in the protein-mineral equilibria. Low viscous liquid products, however, are mostly appreciated by patients, which makes it challenging to formulate such products. Also, a low viscosity is required for a nutritional composition being suitable for tube administration.

Therefore, the problem underlying the present invention is to provide an enteral liquid nutritional composition, either as a supplement, or as a complete nutrition, comprising a high amount of an intact protein, in particular micellar casein, as major protein source, in the smallest volume of liquid, having a low viscosity after heat treatment, and which supports nutrition and well-being in the different patient groups mentioned above, in particular to an elderly person, a person that is in a disease state, a person that is recovering from a disease state, a person that is malnourished, or a healthy person such as a sportsman or sportswoman or an active elderly.

A further problem is to provide a process for the heat treatment of a enteral liquid nutritional composition comprising a high amount of an intact protein, in particular micellar casein, during which treatment the viscosity of said composition does not increase, or not significantly increase, such that a heat treatment process can be used in a larger time/temperature window, i.e. for a longer time and/or at a higher temperature than currently available in the art.

A further problem is to provide an enteral liquid nutritional composition comprising a high amount of an intact protein, in particular micellar casein, with a high heat stability, in particular measured as heat coagulation time.

Casein micelles, as can be found in micellar casein, are remarkably stable against heat. Their stability is maintained by hydrophobic and electrostatic interactions, colloidal calcium phosphate (CCP), and steric effects of protruding chains of κ-casein. Nevertheless, physical and chemical changes occur in the casein micelles during heating of milk due to shifts in the salt equilibria. Heating induces aggregation, which is the first step to instability. This is often reversible. However, subsequently the aggregates may coagulate, thus forming irreversible aggregates, also called coagulates. The changes in salt equilibria become partly irreversible with heating above 120° C., such as with sterilization at ultra-high temperature; they include alterations in structure and composition of the original micellar calcium phosphate into a more insoluble form. Other irreversible changes that occur during heating are hydrolysis of phosphoserine residues, degradation of lactose, and release of κ-casein from the micelle.

Upon heating, coagulation becomes visible when large aggregates have emerged or when a gel is formed. In the art, the resistance of milk, in particular milk protein, against coagulation during heating is called heat stability. The time needed for coagulation is called the 'heat coagulation time', abbreviated HCT (Walstra, P., Wouters, J. T. M., & Geurts, T. J. (2006) *Dairy science and technology* Boc Raton, USA: CRC press). The HCT of milk is highly dependent on pH, as pH affects the protein charge, the amount of CCP in the micelle, and the concentration of free calcium ions in the serum phase. Moreover, the HCT is influenced by the type of milk, because the HCT as function of pH is considerably different for Type A and B milk. The HCT of concentrated milk (7.0-9.0 weight % protein) is much lower than for non-concentrated milk.

The heat stability of (concentrated) milk can be manipulated by addition of calcium chelators, as it is known to affect the concentration of free calcium ions and thereby the integrity of the micellar structure. Phosphates and citrates are commonly used in the dairy industry as heat stabilizers. Orthophosphate and citrate produce a slightly different increase in heat stability because of precipitation of calcium orthophosphate complexes on the micelles and precipitation of calcium citrate complexes in the serum phase. Polyphosphates, such as sodium hexametaphosphate and sodium phytate, increase the heat stability of milk by binding to positively charged amino acids of the casein micelle. Calcium chelators might also, at high chelator concentration, decrease the heat stability of a milk system, as they can chelate a critical level of CCP from the casein micelle at which the integrity of the micellar structure is lost.

The heat stability of normal milk, concentrated milk, evaporated milk, and artificial casein micelle systems has been extensively studied. However, to our knowledge, no studies have systematically evaluated the heat stability of commercial concentrated micellar casein solutions (MCI) at pasteurization or sterilization conditions, for example for a retort sterilization for 20 minutes at 270° C., and for a number of phosphate-based heat stabilizers. An advantage of using micellar casein solutions, such as prepared from MCI powder, instead of concentrated milk is that it contains a small to negligible amount of whey protein. Moreover, although there is general consensus that phosphates and citrate enhance heat stability of milk systems, it is known that the effectiveness with which they do this, differs considerably depending on the source of protein applied.

Unpublished PCT/NL2011/050168 discloses the use of one or more chelating agents selected from the group consisting of a phosphoric acid, citric acid, a soluble phosphate salt, a soluble citrate salt, or a mixture thereof, for independently controlling the viscosity and the transparency of an aqueous micellar casein composition comprising 6 to 20 g/100 ml of micellar casein, and having a pH of about 6 to 8. Heat stability is not addressed.

PRIOR ART

The effect of phosphates and citrate on physical changes of milk solutions is mainly studied in skim milk systems, where about 20% of the protein is whey, with low concentration factors (maximally ~6.5% w/v protein), and relatively low phosphate or citrate levels. Several of these studies focused on milk gels or on age gelation.

U.S. Pat. No. 5,683,984 discloses an enteral tube feeding composition with a native micellar casein protein component. Viscosity issues are identified, and addressed in WO 2009/072885, which discloses a high-energy and high-protein liquid enteral nutritional composition that contains micellar casein and caseinate, and optionally a small amount of whey.

Liang et al. (Nippon Nogei Kagaku Kaishi (1974), 48(1), 49-56) describe the effects of glycerophosphate on gelation of casein micelles and on turbidity in skimmed milk (containing about 3 g/100 ml of casein micelles).

WO 01/72135 A1 (Australian Food Industry Science Center) and U.S. Pat. No. 6,455,082 B1 (Nestec) deal with the addition of phosphates to milk in order to stabilize the milk (containing about 3 g/100 ml of casein micelles). Although they disclose an effect on viscosity, they do not teach an effect in a high-protein system, which is much more critical than a low-protein system such as milk with regard to viscosity.

DETAILED DESCRIPTION OF THE INVENTION

Surprisingly, the inventors have now identified nucleotides as a new kind of phosphate-based heat stabilizers with superior heat stabilization behaviour in a micellar casein composition comprising 6 to 20 g per 100 ml of micellar casein, and having a pH of about 6 to 8, as compared to the commonly used heat stabilizers. The surprising effects are demonstrated in the accompanying experimental section and Figures. Hence, the invention relates to the use of one or more nucleotides for improving (i.e. increasing) the heat stability during a heat treatment of an aqueous micellar casein composition comprising 6 to 20 g per 100 ml of micellar casein, and having a pH of about 6 to 8.

By "improvement of heat stability" in the context of the invention it is preferably understood that the composition remains longer low-viscous and/or lacks formation of aggregates during prolonged heating. The skilled person is given guidance to determine the heat stability using the HCT parameter introduced to this end in the art.

One method to determine the heat coagulation time is falling-ball viscometry, for instance using the Klaro-graph. This method is described in more detail for instance in Van Mil et al (1992). Netherlands Milk and Dairy Journal, 40, 351-368, describing the Klaro-graph as an objective method for continuous assessment of the increased apparent viscosity of coagulating milk. The increase in the apparent viscosity is related to the appearance of the first flocs and so to heat stability as indicated by HCT.

Other methods however exist to determine HCT, mostly based on visual observation, such as the so-called 'Australian Standard Method' and 'Irish Dairy Board method', where samples are heated in glass bottles or tubes in an oil bath until visual coagulation appears (Lehmann and Buckin, "*Determination of the heat stability profiles of concentrated milk and milk ingredients using high resolution ultrasonic spectroscopy*" Journal of Dairy Science, vol99, p 3121-3129 (2005)).

Other methods are based on changes in the amount of nitrogen or on the resistance of a body in a cylinder to aggregates of coagulated milk, such as the Klarograph method. These methods are considered interchangeably, meaning that the HCT parameter found with one method can be readily converted into the HCT parameter as determined with another method.

In one embodiment, it is preferred that the improvement involves an increase in the HCT value of at least 10%, preferably at least 20%, more preferably at least 40%, even more preferably at least 60%, most preferably at least 80%, in particular at least 100%, compared to the reference (not including any chelators, particularly not the one or more nucleotides of the invention).

A nucleotide is composed of a nucleobase (nitrogenous base), a five-carbon sugar (either ribose or 2'-deoxyribose), and one to three phosphate groups. Together, the nucleobase and sugar comprise a nucleoside. The phosphate groups form bonds with either the 2, 3, or 5-carbon of the sugar, most commonly with the 5-carbon site. Ribonucleotides are nucleotides where the sugar is ribose, and deoxyribonucleotides contain the sugar 2'-deoxyribose (such as in thymidine). In the context of the invention, the nucleotides can contain either a purine, pyrimidine or hypoxanthine base. Purine bases are adenine and guanine, pyrimidine bases are thymine, cytosine or uracil. A large benefit of the nucleotides according to the invention is that they are commercially available in food grade quality, either as separate compounds or as a mixture. The phosphate group of the nucleotide determines for a very large part the stability of the complexes formed with cations.

According to one embodiment, the nucleotide is a ribonucleotide. The ribonucleotide can be a purine-based ribonucleotide, most preferably a purine-based monophosphate ribonucleotide.

According to a preferred embodiment, the ribonucleotide is a pyrimidine-based ribonucleotide, preferably based on uracil or cytosine, more preferably based on uracil.

According to another embodiment, the nucleotide is selected from the group of uridine monophosphate (UMP), cytidine monophosphate (CMP), thymidine monophosphate (TMP), guanosine monophosphate (GMP), adenosine monophosphate (AMP), and inosine monophosphate (IMP). The nucleotide is preferably uridine monophosphate (UMP) or cytidine monophosphate (CMP), most preferably UMP.

According to another embodiment, the nucleotide is selected from the group of uridine diphosphate (UDP), cytidine diphosphate (CDP), thymidine diphosphate (TDP), guanosine diphosphate (GDP), adenosine diphosphate (ADP), and inosine diphosphate (IDP). The nucleotide is preferably uridine diphosphate (UDP) or cytidine diphosphate (CDP), most preferably UDP.

According to another embodiment, the nucleotide is selected from the group of uridine triphosphate (UTP), cytidine triphosphate (CTP), thymidine triphosphate (TTP), guanosine triphosphate (GTP), adenosine triphosphate (ATP), and inosine triphosphate (ITP). The nucleotide is preferably uridine triphosphate (UTP) or cytidine triphosphate (CTP), most preferably CTP.

In the above embodiments, the phosphate salt is preferably a sodium salt, a potassium salt, or a mixture thereof, preferably a sodium salt. These salts are preferred for the development of nutritional compositions as they introduce metals as counter ions (e.g. sodium or potassium) which are essential in a normal diet. It is understood that—in practice—a product does not always contain an equimolar amount of metal counter ions, relative to the phosphoric acid, although the product is designated as such. Such products are also comprised within the definition of the phosphate salts according to the invention.

According to one embodiment, the counter ion (e.g. sodium or potassium) is present in an amount less than or equal to an equimolar amount, relative to the acid. For example, one molecule of inositol hexaphosphate may contain 1 to 12 counter ions, and the product inositol hexaphosphate may therefore contain molecules with different number of counter ions, such that the total equivalent of counter ions in the product is smaller than or equal to the total equivalent of inositol hexaphosphate.

According to a preferred embodiment, the nucleotide is disodium uridine monophosphate, tetrasodium uridine diphosphate, hexasodium uridine triphosphate, more preferably disodium uridine monophosphate.

The nucleotide are readily dissolved in the aqueous micellar casein composition at pH 6 to 8.

The nucleotide(s) is(are) preferably added in an amount ranging from 1 to 120 mEq.L$^{-1}$ of said nucleotide, preferably 5 to 100 mEq.L$^{-1}$, more preferably 10 to 80 mEq.L$^{-1}$, most preferably 20 to 60 mEq.L$^{-1}$, in order to render the claimed effects. Hence, the heat-treated aqueous micellar casein composition comprises an amount of 1 to 120 mEq.L$^{-1}$, preferably 5 to 100 mEq.L$^{-1}$, more preferably 10 to 80 mEq.L$^{-1}$, most preferably 20 to 60 mEq.L$^{-1}$ of one or more nucleotides.

Preferably, the heat-treated aqueous micellar casein composition according to the invention comprises at least 6, 7, 8, 9, 10, 11, 12, 13, 14, 15, 16, 17, 18 or 19 g and at most 20 g of micellar casein per 100 ml of composition, preferably 11 to 18 g/100 ml, more preferably 12 to 18 g/100 ml, and most preferably 14 to 18 g/100 ml.

Preferably, the micellar casein protein is an intact protein. In the context of this invention, "non-hydrolysed" proteins is equivalent to "intact" proteins, meaning that the proteins have not, or not substantially, been subjected to a hydrolysis process. However, minor amounts of hydrolysed proteins may be present in the source of non-hydrolysed proteins, or may be added to the formulation, such as additional amino acids, such as for example branched chain amino acids, for example leucine, isoleucine, valine and the like. In this context, "minor" should be understood as an amount of about 10 weight % or less, preferably less than 5 wt %, based on total protein.

In the context of this invention, it is understood that "liquid" or "aqueous" refers to a water-based composition, such as a solution or a suspension, having a viscosity of 200 mPa·s or less, as determined at 20° C. in a rotational rheometer at a shear rate of 50 s$^{-1}$. A value of about 200 mPa·s is herewith defined as an empirical upper viscosity limit, above which a liquid system has an unacceptably high viscosity to be readily drinkable. It is preferred to provide a composition having a viscosity of less than 200 mPa·s, more preferably 150 mPa·s or less, more preferably 120 mPa·s or less, more preferably 100 mPa·s or less, more preferably 80 mPa·s or less, most preferably 50 mPa·s or less.

Preferably, all or a major part of the protein of the heat-treated aqueous micellar casein composition comprises micellar casein, preferably at least 80 wt %, including protein sources providing the 80:20 casein:whey ratio. In a preferred embodiment the heat-treated aqueous micellar casein composition comprises micellar casein in an amount of at least 85 weight %, even more preferably at least 90 weight %, most preferably at least 95 weight % of micellar casein. The weight contribution of optional hydrolysed protein and amino acids are accounted for in the total protein weight. In one preferred embodiment, micellar casein is present in an amount of 85-100 wt % of all proteinaceous matter.

Within the context of the present invention, the term "heat treatment" is meant to comprise any method using heat (preferably sterilization, pasteurization) to reduce the number of or remove possible pathogens. Preferably, a heat treatment includes a heat treatment at a high temperature for a short period, such as a UHT (Ultra High Temperature) treatment.

In one embodiment, the heating conditions are selected in line with those presented in WO-A-03/-11040, its contents herein incorporated by reference. The heat treatment is preferably a temperature of at least 60° C., preferably at least 70° C., and less than 200° C., more preferably less than 160° C., for a period of time equal to or at least t, which period of heating t is governed by the following formula:

$$t=(500/(T-59))-4,$$

in which t is the duration of heating (in seconds) and T is the heating temperature (in ° C.). More preferably, the maximum heating conditions complied are governed by the following formula:

$$t=(90000/(T-59))-900,$$

in which t and T have the aforesaid meaning. The heat treatment preferably involves a period of 0.1 sec to 24 hour. It is particularly preferred that the heating time ranges from 10 s–1 hour, more preferably from at least 10 minutes. The preferred corresponding minimum and maximum temperatures may be calculated from the above formulae.

Additionally or alternatively, the "heat treatment" is characterized by a minimum 'sterilizing value' or 'F-zero' (F0) value of at least 2.8 (min), more preferably at least 3 min, most preferably at least 4 minutes, in particular at least 4.5 minutes. It is a standardized and FDA-approved parameter. For any time temperature combination, the sterilizing value F0 is the equivalent minutes at 250° F. At F0=2.8 min, *Clostridium Botulinum* is inactivated.

In one embodiment, the preferred heat treatment is sterilization or pasteurization, both having technical meanings well-established in the art. Henceforth, within the context of the present invention, pasteurization is comprised within the term sterilization. Within the context of the present invention, a "heat-treated composition" is a composition that is obtained or obtainable by subjecting a composition to a sterilization treatment. In general, the quantity of potentially pathogenic micro-organisms of the sterilized composition meets food safety requirements, as applicable e.g. in the US or EU. In particular, a heat-treated composition in accordance with the invention maintains to meet such requirement, for at least 6 months, preferably at least 12 months after packaging, at the beginning of shelf life, when stored in a sealed packaging at ambient temperature (20° C.). It is particularly preferred that changes in stability, e.g. the viscosity, are insignificant over such period, preferably less than 10% change, more preferably less than 5% change.

The pH of the heat-treated aqueous micellar casein composition should be between about 6 and 8. The pH is determined in the aqueous micellar casein composition and this can be done by routine methods, known to the skilled person, such as using a commercially available pH metering device.

Micellar casein, sometimes also referred to as "native" micellar casein, refers to casein in the form of micelles, which is the native form of casein in milk. It is a high quality milk protein and naturally occurring in milk in a concentration of about 2.6 g/100 ml. It is concentrated by a process that does not, or does not substantially denature the casein proteins and it is marketed as Micellar Casein Isolate (MCI) in powder form. Fresh skim milk is subjected to a microfiltration process, in much the same process used to concentrate whey protein, to produce a pure, substantially undenatured milk protein with its native structure. The resulting material contains between 90% and 100%, preferably more than 95% by weight of micellar casein on dry matter, the remainder being whey protein, non-protein nitrogen and other constituents, such as lactose and inorganic salts, in particular calcium phosphate. The casein micelles generally have a hydrodynamic radius of 40 to 400 nm, a molecular weight of 106 to 109 kDa and a calcium: phosphorous weight ratio of 1.4 to 2.4, the calcium-content being very high, in the order of about 25 g/kg protein. It has an intrinsic low viscosity and a liquid composition comprising said MCI is therefore easy to drink. The amount of monovalent metal ions, in particular Na and K, is very low, typically in the range of about 1 to 2 g/kg protein.

In contrast, caseinate refers to the curd form of casein, having lost its native micellar structure. It is bound to a metal, such as sodium, potassium, calcium and magnesium.

Within the context of this invention, it is understood that micellar casein may also be provided by other milk protein sources, such as, for instance, sources which essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk. The micellar casein may also be provided in liquid form via an ultrafiltrate or microfiltrate.

Nutritional Composition

The heat-treated aqueous micellar casein composition may further contain other nutritional components, such as a fat source, a digestibe carbohydrate source, and a non-digestible carbohydrate source, as well as vitamins, minerals and the like. The nutritional composition is obtainable or obtained by a manufacturing process in which it has been subjected to heat treatment (preferably sterilized or pasteurized) in the presence of one or more nucleotides according to the invention.

In a preferred embodiment, the invention is directed to a nutritional composition comprising 6 to 20 g, preferably 9 to 20 g, of protein per 100 ml of the composition and having a pH of about 6 to 8, in which all or a major part of said protein comprises micellar casein, comprising one or more nucleotides according to the invention. The amount of nucleotide(s) added to the composition preferably ranges from 1 to 120 mEq.L$^{-1}$, preferably 5 to 100 mEq.L$^{-1}$, more 10 to 80 mEq.L$^{-1}$, most preferably 20 to 60 mEq.L$^{-1}$. The nucleotide(s) could be selected in accordance with one or more of the embodiments described above.

Preferably, the nutritional composition according to the invention comprises at least 9, 10, 11, 12, 13, 14, 15, 16, 17, 18 or 19 g and at most 20 g of protein per 100 ml of composition, preferably 11 to 18 g/100 ml, more preferably 12 to 18 g/100 ml, and most preferably 14 to 18 g/100 ml, in which all or a major part of said protein comprises micellar casein.

In the context of this application, the wording "all or major part" in relation to micellar casein should be interpreted as an amount of micellar casein which ranges from 70 to 100% of the total protein, preferably 80-98%, more preferably 90-95%. The term 'total protein' also includes optional hydrolysed proteins and amino acids.

According to another embodiment of the present invention, the nutritional composition of the invention comprises optionally 0-30 weight %, preferably 1-30 wt %, more preferably 2-20 wt %, most preferably 5-10 wt % of caseinate, based on the total weight of the protein.

According to another embodiment of the present invention, the protein provides 10% to 100%, preferably 20% to 80%, more preferably 30% to 70%, most preferably 30% to 60% of the total energy content of the composition. The '% of total energy content' is also abbreviated as En %; En % is thus short for energy percentage and represents the relative amount that a constituent contributes to the total caloric value of the composition. The high levels of protein are beneficial for patients who may not be physically capable of receiving a large volume, for example, fluid restricted patients. Such patients can be given a reduced level of fluid while still receiving a required amount of nutritional support per day. The composition may be used as a complete nutrition, in addition to or as a replacement for a normal meal consumption. The composition may also be used as a supplement, in addition to normal meal consumption, when the uptake of fats and carbohydrates is of less concern.

According to another embodiment of the present invention, the nutritional composition has an energy density of at least 0.36 kcal/ml, more preferably at least 1.0 kcal/ml, particularly at least 1.5 kcal/ml of composition, more in particular at least 2.0 kcal/ml.

Although the composition has a high energy density, by using the nucleotides according to the invention, it may also have a sufficiently low viscosity to allow it to be consumed by persons that may have difficulty swallowing large amounts of liquid or those that are tube fed. Hence, in one embodiment, the nutritional composition is a liquid, preferably having a viscosity of less than 200 mPa·s, preferably less than 80 mPa·s, preferably less than 70 mPa·s, more preferably 50 mPa·s, still more preferably less than 40 mPa·s, most preferably equal to about 20 mPa·s, as determined at 20° C. in a rotational rheometer at a shear rate of 50 s$^{-1}$.

In one embodiment of the present invention, the amount of micellar casein in the nutritional composition according to the invention is at least 70 weight %, preferably at least 80 weight %, more preferably at least 90 weight %, more preferably at least 95 weight % and at most 100 weight % of the total protein present in the nutritional composition.

As aforementioned, the nutritional composition of the present invention should not contain large amounts of proteins other than micellar casein and, according to one embodiment, optionally at most 30 weight % of caseinate. In a further embodiment of the present invention, the nutritional composition may comprise 0-15 weight % of whey, preferably 0.5-10 weight % of whey, more preferably 1 to 10 wt % of the total protein present in the nutritional composition; in one embodiment, the composition comprises less than or equal to 5 weight % of whey of the total protein present in the nutritional composition.

In one embodiment of the present invention, the weight ratio of micellar casein to caseinate ranges from about 100:0 to about 70:30. Preferably, the weight ratio of micellar casein to caseinate ranges from about 80:20 to about 100:0.

The nutritional composition according to the invention is designed to either supplement a person's diet or to provide complete nutritional support. Hence, the composition according to the invention may further comprise at least fat and/or carbohydrate and/or a source of vitamins, minerals, trace elements and/or a source of indigestible carbohydrates. Preferably, the composition according the invention is a nutritionally complete composition.

In one embodiment, the invention pertains to a method of providing nutrition to a person in need thereof, comprising the steps of administering to said person the nutritional composition as described here. The person is preferably an elderly person, a person that is in a disease state, a person that is recovering from a disease state, a person that is malnourished, or a healthy person such as a sportsman or sportswoman or an active elderly. In this respect, it is submitted that in the context of this application, an elderly person is a person of the age of 50 or more, in particular of the age of 55 or more, more in particular of the age of 60 or more, more in particular of the age of 65 or more.

Fat

In one embodiment the present liquid enteral nutritional composition further comprises fat. The amount of fat may range between 5 and 95%, preferably between 10 and 70%, more preferably between 20 and 40%, relative to the total energy content of the composition.

With regard to the type of fat, a wide choice is possible, as long as the fat is of food quality. The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil and/or sunflower oil.

The fat may include a source of medium chain fatty acids, such as medium chain triglycerides (MCT, mainly 8 to 10 carbon atoms long), a source of long chain fatty acids, such as long chain triglycerides (LCT) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

In one specific embodiment, the fat comprises 30 to 60 weight % of animal, algal or fungal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil is used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexaenoic acid (DHA), i.e. less than 6 weight %, preferably less than 4 weight % based on total fat. Marine oils containing DHA are preferably present in the composition according to the invention in an amount lower than 25 weight %, preferably lower than 15 weight % based on total fat. On the other hand, inclusion of eicosapentaenoic acid (EPA) is highly desirable for obtaining the maximum health effect. Therefore, in another embodiment, the amount of EPA may range between 4 weight % and 15 weight %, more preferably between 8 weight % and 13 weight % based on total fat. The weight ratio EPA:DHA is advantageously at least 6:4, for example between 2:1 and 10:1. In yet another embodiment, the amount of EPA is very low, such as 0.1 to 1 weight %, preferably 0.3 weight % or 0.6 weight %, based on total fat.

Also, the nutritional composition according to the invention may beneficially comprise an emulsifier. Commonly known emulsifiers may be used and generally the emulsifier contributes to the energy content of the fat in said composition.

Digestible Carbohydrate

In one embodiment of the present invention, the nutritional composition according to the invention further comprises a digestible carbohydrate. Preferably, the digestible carbohydrate provides between 30 to 60% of the total energy content of the composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and polysaccharides.

The composition of the digestible carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the digestible carbohydrates between 1.5 and 6, preferably between 1.8 and 4. In order to avoid excessive sweetness, the total level of sucrose and fructose is preferably less than 60%, more preferably less than 52%, more preferably less than 40% of the weight of the carbohydrate, especially of the digestible carbohydrate. Long-chain digestible carbohydrates such as starch, starch fractions and mild starch hydrolysates (DE>1, DE<20), may also be present, preferably in an amount of less than 25 weight %, especially less than 15 weight % of the digestible carbohydrate, and less than 6 g/100 ml, preferably less than 4 g/100 ml of the total enteral liquid nutritional composition according to the invention.

In one embodiment of the present invention, the digestible carbohydrate includes maltodextrose (i.e. glucose polymer) with a high DE (dextrose equivalent). In one embodiment the digestible carbohydrate includes maltodextrose with a DE of >10, preferably a DE of >20, more preferably >30 or even >40, such as a DE of about 47. In one embodiment of the present invention, the digestible carbohydrate includes maltodextrose with a DE>10 and sucrose.

Surprisingly, the use of maltodextrose leads to few or no Maillard reaction products upon heating. Without being bound to any explanation, this effect might be attributed to the fact that the compact micellar structure of the micellar casein offers few lysine reaction sites for a Maillard reaction. In one embodiment of the present invention, the digestible carbohydrate includes maltodextrose with a high DE in an amount of at least 35 weight %, preferably at least 50 weight %, preferably at least 65 weight %, preferably at least 90 weight % of the total weight of digestible carbohydrate. In one embodiment of the present invention, the digestible carbohydrate includes maltodextrose with a low DE of 2 to 20. In one embodiment of the present invention, the digestible carbohydrate includes maltodextrose with a low DE of 2 to 10, preferably with a low DE of about 2. In one embodiment of the present invention, the digestible carbohydrate includes maltodextrose with a low DE in an amount of less than 35 weight %, preferably less than 20 weight %, preferably less than 10 weight % of the digestible carbohydrate. Maltodextrose with a low DE may also be referred to as maltodextrine. In another embodiment of the present invention, the digestible carbohydrate includes maltodextrose with a high DE, preferably a DE of >20, preferably >30 or even >40, most preferably a DE of about 47 in combination with maltodextrose with a low DE, preferably a low DE of 2 to 20, more preferably a low DE of 2 to 10, most preferably with a low DE of about 2. As is known, maltodextrose with a low DE, such as of about 2, gives rise to a high viscosity. Maltodextrose with a high DE, such as of about 47 gives rise to a low viscosity, but is very sweet. The combination of both maltodextroses optimizes the balance between sweetness and viscosity. In one embodiment of the present invention, the digestible carbohydrate includes at least 65 weight %, preferably at least 90 weight %, based on total weight of digestible carbohydrate of maltodextrose with a DE>40, preferably with a DE of about 47 and 0 to 10 weight % of maltodextrose with a DE 2 to 10, preferably with a DE of about 2.

In another embodiment of the present invention, the digestible carbohydrate includes trehalose. It is one of the main objects of the invention to provide a nutritional composition with a low viscosity. Sucrose is very well suited for such purpose, but gives rise to very sweet compositions, which are in general disliked by the consumer. Maltodextrose with a low DE, such as of about 2, does not suffer from the latter drawback, but gives rise to a high viscosity. Maltodextrose with a high DE, such as of about 47 gives rise to a low viscosity, but is again very sweet, and gives further rise to the undesired Maillard reactions. Trehalose is a preferred choice of carbohydrate, as it gives rise to a low viscosity, no undesired Maillard reactions and it has a sweetness about half of that of sucrose. In one embodiment of the present invention, the digestible carbohydrate includes trehalose in an amount of 20% to 60% of the weight of the carbohydrate, in an amount of 20% to 45%, more preferably in an amount of 25% to 45% of the weight of the digestible carbohydrate.

Vitamins, Minerals and Trace Elements

The composition according to the invention may contain a variety of vitamins, minerals and trace elements.

In one embodiment of the present invention, the composition according to the invention provides all necessary vitamins, most of the minerals and trace elements. For example, the composition according to the invention preferably provides 6 mg of zinc per 100 ml of the composition which is beneficial for tissue repair in a healing patient. Preferably, the composition according to the invention (also) provides 25 mg of vitamin C per 100 ml of the composition to aid patients with more severe healing requirements. Further, preferably, the composition according to the invention (also) provides 2.25 mg iron per 100 ml of the composition. Iron is beneficial in maintaining bodily fluids as well as circulatory system functions in an elderly patient.

The invention implicates that a composition according to the present invention may contain sodium and/or potassium levels outside FSMP (Foods for Special Medical Purposes) legislation levels.

Non-Digestible Carbohydrates

The enteral liquid nutritional composition according to the invention may optionally be fortified with non-digestible carbohydrates (dietary fibres) such as fructo-oligosaccharides or inulin. In an embodiment of the present invention, the composition according to the invention comprises 0.5 g/100 ml to 6 g/100 ml of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylooligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, and/or below 0.6 g/100 ml. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 ml. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructooligosaccharides or galactooligosaccharides, which may also contain a small amount of higher saccharides (e.g. with a DP of 11 to 20). Such oligosaccharides preferably comprise 50 weight % to 90 weight % of the fibre fraction, or 0.5 g/100 ml to 3 g/100 ml of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety. More in particular, the acid oligosaccharide has a degree of polymerization (DP) between 1 and 5000, preferably between 1 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, beta-D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxohexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl(1-6)-α-D-glucopyranosyl-β-D-fructofuranoside), β-galactooligosaccharides or transgalactooligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosylsynthetic galactooligosaccharide (neogalactobiose, isogalactobiose, galsucrose, isolactose I, II and III), fructans—Levan-type (β-D-(2→6)-fructofuranosyl)$_n$α-D-glucopyranoside), fructans—Inulin-type (β-D-((2→1)-fructofuranosyl)$_n$-α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosachararides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin, alginate, and mixtures thereof; and a neutral oligosaccharide, selected from the group consisting of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect.

Preferably the composition according to the invention comprises:

an acid oligosaccharides as defined above;
a galactose-based neutral oligosaccharide (of which more than 50% of the monose units are galactose units), preferably selected from the group consisting of galactooligosaccharide and transgalactooligosaccharide; and
a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

The mixture of acid- and neutral oligosaccharides is preferably administered in an amount of between 10 mg and 100 gram per day, preferably between 100 mg and 25 grams per day, even more preferably between 0.5 and 20 gram per day.

Viscosity and Osmolarity

In the context of this invention, the viscosity is preferably measured in a rotational rheometer using a plate-and-cone geometry at 20° C. at a shear rate of 50 s$^{-1}$. However, alternatively cup-and-bob geometry may be applied.

In one embodiment of the present invention, the viscosity of the enteral liquid nutritional composition is less than 200 mPa·s, more preferably less than 150 mPa·s, more preferably less than 120 mPa·s, more preferably less than 100 mPa·s, more preferably less than 80 mPa·s, and most preferably 50 mPa·s. A low viscosity is ideal for orally administering the enteral liquid nutritional composition according to the invention because a person may easily consume a serving having a low viscosity such as that displayed by the present invention. This is also ideal for unit dosages that are tube fed.

In another embodiment of the present invention, the low-viscosity composition may be used a basis for the manufacturing of an enteral liquid nutritional composition having a viscosity of more than 200 mPa·s, more preferably more than 400 mPa·s, more preferably more than 600 mPa·s. A high viscosity is ideal for producing a pudding, a gel, or a semi-solid or semi-liquid composition. This is also ideal for unit dosages that are spoonable.

In one embodiment of the present invention, the osmolarity of the composition is preferably lower than 1200 mOsm/l, more preferably lower than 900 mOsm/l, more preferably lower than 800 mOsm/l, and most preferable lower than 700 mOsm/l.

Dosage Unit

The enteral liquid nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units, e.g. from 4 (250 ml/unit) to 40 (20 ml/unit) per day for an energy supply of 2000 kcal/day using a enteral liquid nutritional composition according to the invention of 2.0 kcal/ml.

The enteral liquid nutritional composition can also be a food supplement, for example to be used in addition to a non-medical food. Preferably as a supplement, the enteral liquid nutritional composition contains per daily dosage less than 1500 kcal, in particular as a supplement, the enteral liquid nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using a enteral liquid nutritional composition according to the invention of 2.0 kcal/ml.

In one embodiment of the present invention, a unit dosage comprises any amount of the enteral liquid nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using an enteral liquid nutritional composition according to the invention of 2.0 kcal/ml. Alternatively a person receiving 125 ml unit dosages can be given 4 or 5 or 6 or 7 or 8 unit dosages per day to provide nutritional support using an enteral liquid nutritional composition according to the invention of 2.0 kcal/ml. Such small dosage units are preferred because of better compliance.

In one embodiment of the present invention, the composition is provided in a ready to use form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the enteral liquid nutritional composition according to the present invention. In one embodiment of the present invention, the present enteral liquid nutritional composition may thus be obtained by dissolving or reconstituting a powder, preferably in an aqueous composition, in particular water.

In one embodiment of the present invention, the composition according to the invention may be used as a basis for the manufacturing of a semi-solid nutritional composition, such as a crème, a pudding, a custard, a soup, an ice cream, or a jelly. To this end, the composition according to the invention is processed to convert the low viscosity composition according to the invention into a more solid or viscous one, e.g. by adding thickeners or gelling agents and further process the mixture into the final product. Thickeners and/or gelling agents can also be present in the formulation from a more earlier stage of the process, or even dissolved together with the nutrients at the beginning of the process.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

EXPERIMENTAL

The following serves to evidence the inventive concepts. However, the invention is not considered tied by any of the theories and hypotheses for explaining the observed phenomena given here below.

The use of simplified concentrated milk systems, instead of complete medical nutrition recipes (i.e. systems containing high concentrations of mono- and divalent ions, carbohydrates, and fat), is an effective way to determine the influence of phosphates on the viscosity of the compositions. We have selected a commercial protein source, namely micellar casein isolate (MCI), which contains a negligible amount of whey protein, and prepared 9% w/v high-protein solutions to which the phosphate compounds in a large concentration range were added.

LIST OF FIGURES

FIG. 1: HCT, calcium-ion activity, viscosity, turbidity, and zeta potential of the MCI solution at pH 6.7 as function of calcium chelator concentration. Results are the means for at least duplicates with standard deviations as error bars. (↑) and (---) indicate that no coagulation appeared after heating for 90 min.

Figure 2:
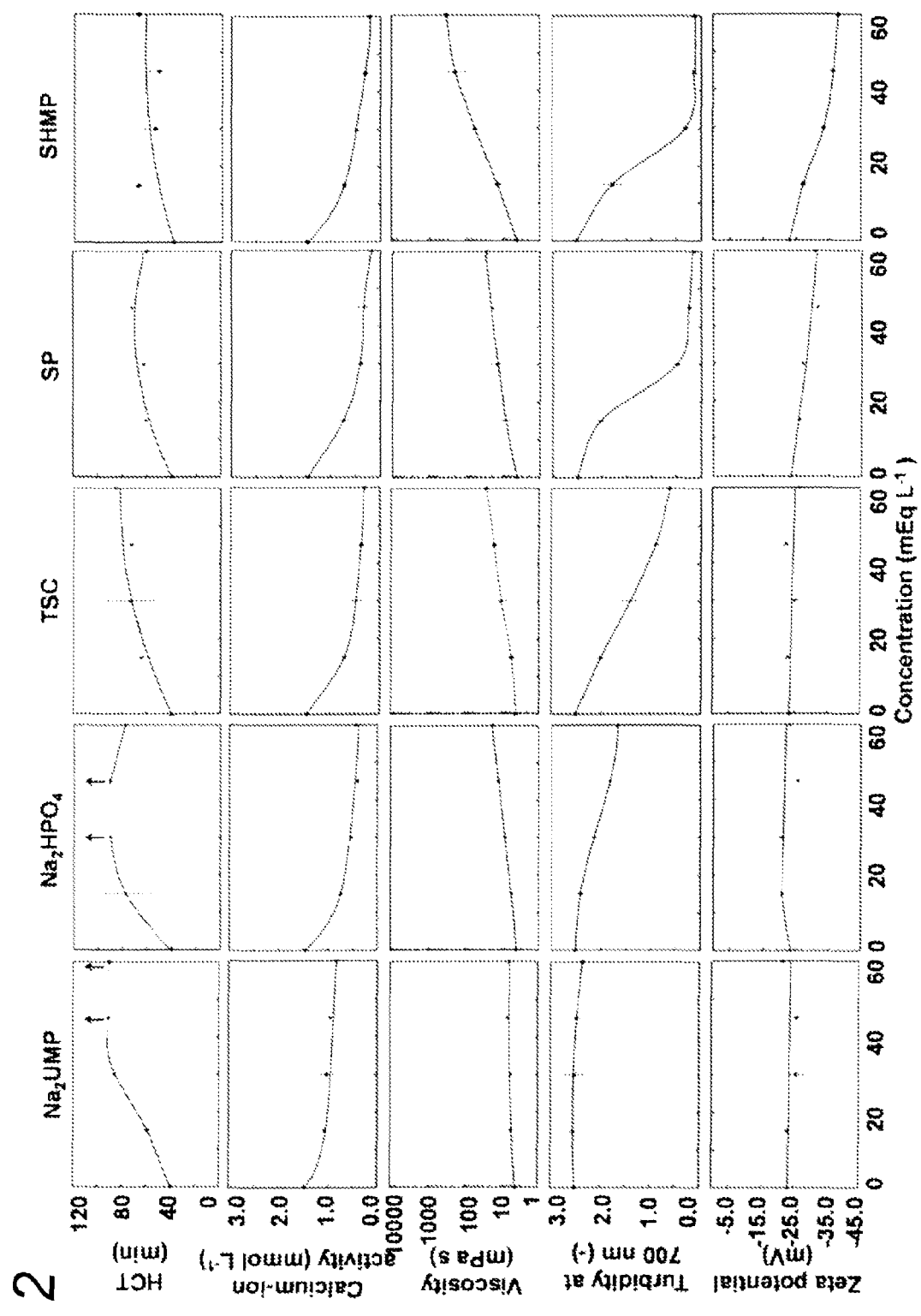

FIG. 2: HCT, calcium-ion activity, viscosity, turbidity, and zeta potential of the MCI solution at pH 7.0 as function of calcium chelator concentration. Results are the means for at least duplicates with standard deviations as error bars. (↑) and (---) indicate that no coagulation appeared after heating for 90 min.

Figure 3:
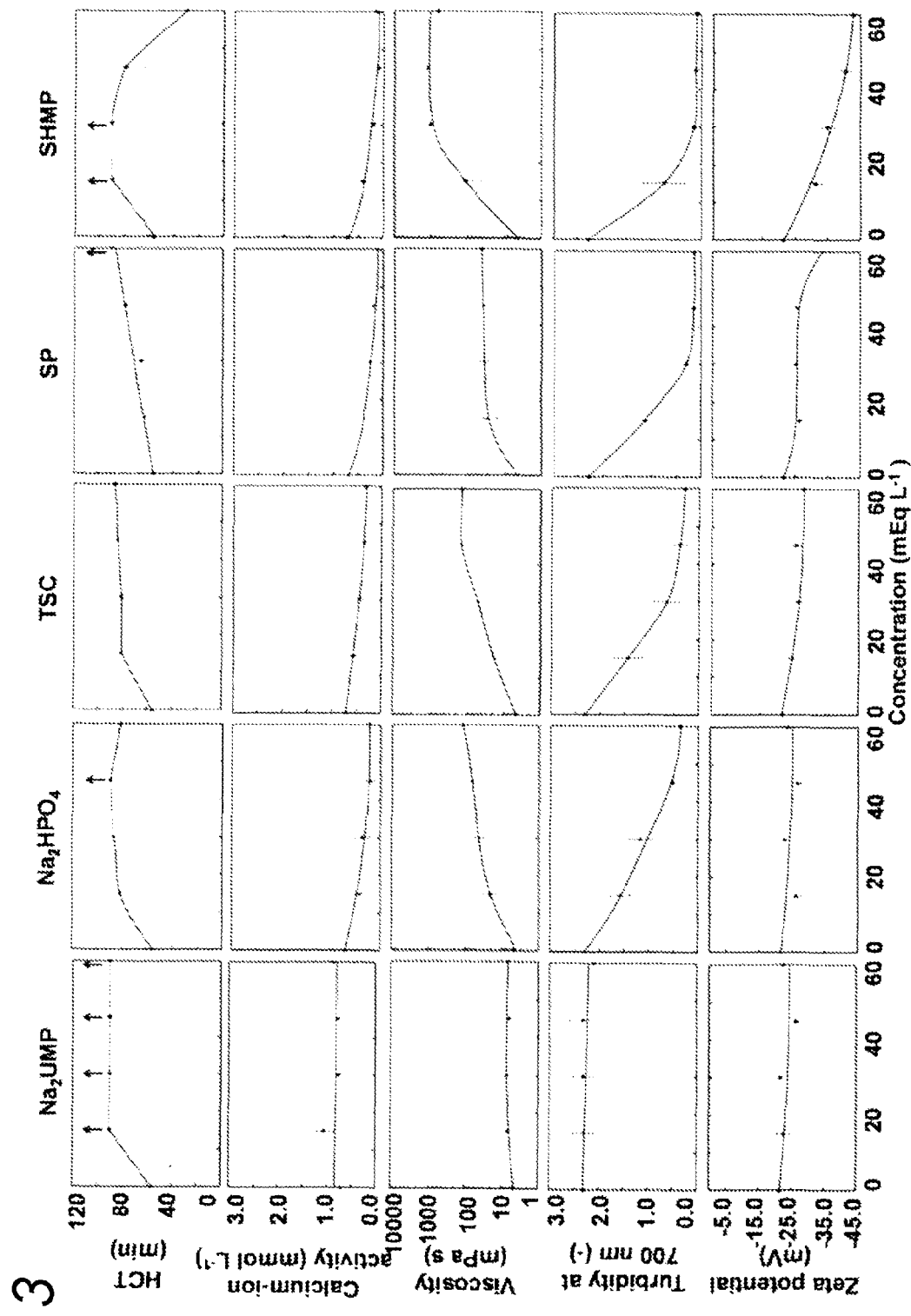

FIG. 3: HCT, calcium-ion activity, viscosity, turbidity, and zeta potential of the MCI solution at pH 7.3 as function of calcium chelator concentration. Results are the means for at least duplicates with standard deviations as error bars. (↑) and (---) indicate that no coagulation appeared after heating for 90 min.

Figure 4:
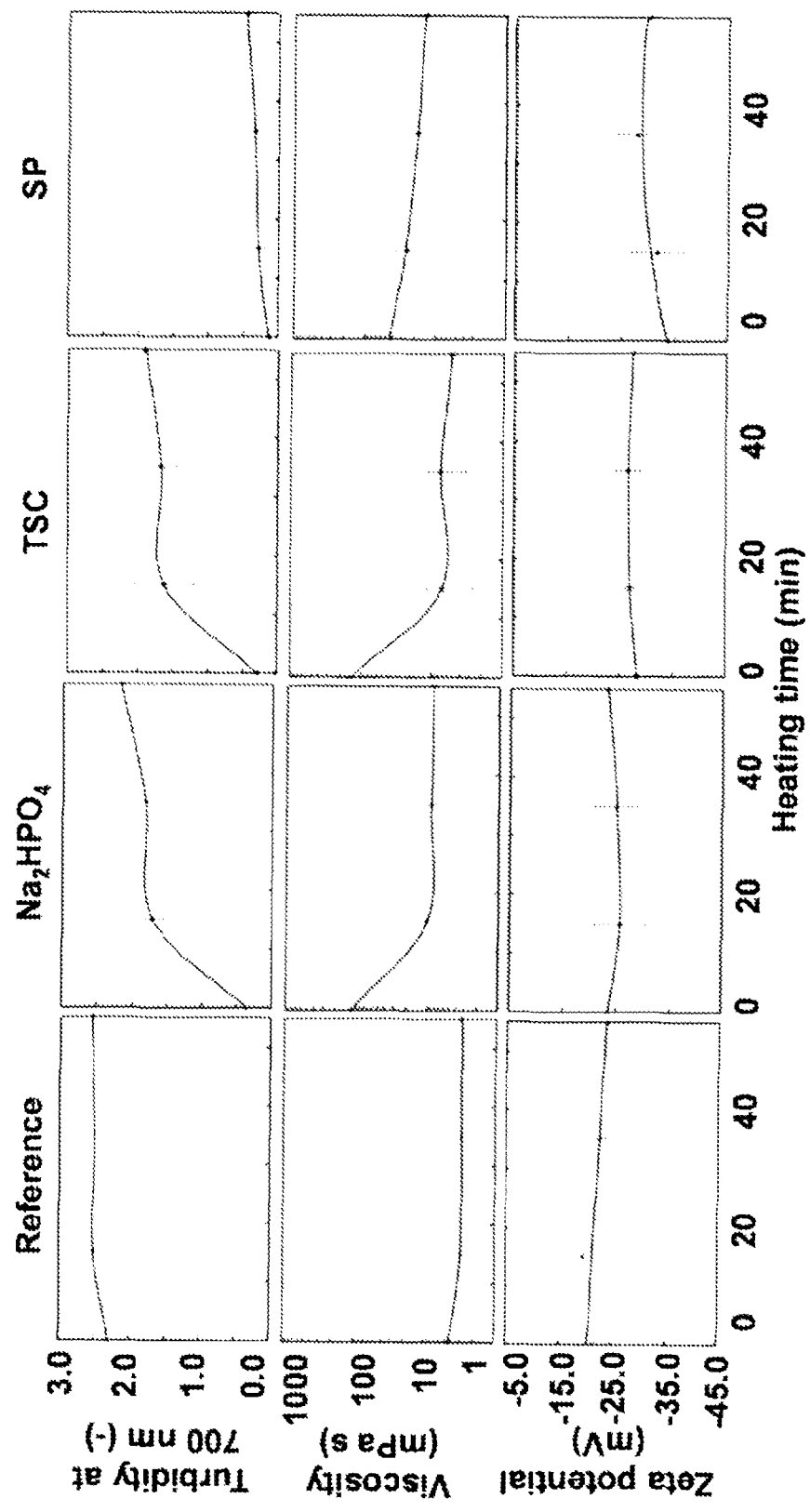

FIG. 4: Turbidity, viscosity, and zeta potential of the MCI solution at pH 7.3 of the reference samples and those with 60 mEq $L^{-1}$ $Na_2HPO_4$, TSC, and SP as function of the heating time in the oil bath. Results are the means for duplicates with standard deviations as error bars.

1. MATERIALS AND METHODS 1.1 Sample Preparation

MCI powder (Nutripro™) was supplied by DairyGold Food Ingredients (Cork, Ireland). This powder contains 85 w/w % protein of which ≤5 w/w % is whey. A MCI solution with 9% w/v protein was prepared by dissolving the MCI powder in 80% of the total demineralised water at ambient temperature, while stirring at 600 rpm with a laboratory stirrer (RW 20.n, IKA Labortechnik, Staufen, Germany). A 9% w/v MCI solution contains approximately 8.5 mmol·L−1 sodium, 4.2 mmol·L−1 potassium, 2.5 mmol·L−1 chloride, 59.8 mmol·L−1 calcium, 43.5 mmol·L−1 phosphorus, and 3.1 mmol·L−1 magnesium. The protein solution was homogenized with a high pressure laboratory homogeniser (NS2006L, GEA Niro Soari S.P.A., Parma, Italy) at 350+50 bar to obtain single casein micelles with a diameter D[4,3] of 0.15 μm as determined with a Mastersizer 2000 containing a hydro 2000G water bath (Malvern Instruments, Worcestershire, England). The temperature of the protein solution was 40° C. after homogenization.

Stock solutions were prepared of disodium uridine monophosphate ($Na_2UMP$) (Yamasa Corporation, Chiba, Japan), disodium hydrogen phosphate ($Na_2HPO_4$) (Merck & Co. Inc, Darmstadt, Germany), sodium hexametaphosphate (SHMP) (VWR International Ltd, Poole, England), phytic acid dodecasodium salt hydrate (SP) (Sigma-Aldrich GmbH, Steinheim, Germany), and trisodium citrate (TSC) (Gadot Biochemical Industries Ltd., Haifa Bay, Israel). Different amounts of these stock solutions were added to the MCI solutions in order to obtain final chelator concentrations of 0, 15, 30, 45, or 60 mEq $L^{-1}$ in the samples. These chelators contain a different amount of negative charges, which gives them different calcium-binding capacities (De Kort, E. J. P., Minor, M., Snoeren, T. H. M., van Hooijdonk, A. C. M., & van der Linden, E. (2009). Journal of Dairy Science and Technology, 89, 283-299). Therefore, the concentration ranges of the calcium chelators were based on milliequivalents so as to add a similar amount of charges to the samples. Only sodium sources were used, because the type of counter-ion may also influence protein-mineral interactions.

The pH of the samples was adjusted, after stirring for 30 minutes, to 6.7±0.05, 7.0±0.05, and 7.3±0.05 with 1 mol $L^{-1}$ sodium hydroxide (Sigma-Aldrich GmbH, Steinheim, Germany) or 1 mol $L^{-1}$ hydrochloric acid (Merck & Co. Inc, Darmstadt, Germany). Finally, samples were brought to their final protein concentration of 9% w/v with demineralized water. Samples were stored overnight at 20° C. for approximately 17 hours to let them equilibrate. The pH of the samples was readjusted the next morning to 6.7±0.05, 7.0±0.05, or 7.3±0.05 in case deviations had occurred during storage. Deviations in pH were always small and samples did not show any visible spoilage. Samples with 0, 15, 30, 45, and 60 mEq $L^{-1}$ phosphate or citrate were analyzed at least in duplicate for their HCT in the Klarograph and samples with 0, 15, and 60 mEq $L^{-1}$ phosphate or citrate were heated for 0, 15, 35, and 55 minutes in an oil bath. The samples were analyzed in duplicate before and after heating in the oil bath for their pH, calcium-ion activity, turbidity, viscosity, and zeta potential.

1.2 HCT Measurements; Klarograph

The Klarograph was used to determine the HCT of the samples. The Klarograph is based on the principle of the falling-ball viscometer (Cruijsen, J. M. M. 1996. Wageningen Agricultural University, Wageningen; De Wit, J. N., Klarenbeek, G., & De Graaf, C. (1986). Voedingsmiddelentechnologie, 19 (3), 25-27; Van Mil, P. J. J. M., & De Koning, J. (1992). Netherlands Milk and Dairy Journal, 40, 351-368). Samples are inserted in the inner part of a double walled glass tube. The inner diameter of the tubes is 9.3 mm and the volume is 20 ml from the bottom to the expansion chamber. Two glass balls with a diameter 9.0 mm are put in the tubes. The tubes are placed in the system and silicone oil is circulated around the tubes. The silicone oil is connected to a thermostatic oil bath, which is set at 126° C. The apparatus allows the use of eight tubes at the same time (2 times 4 tubes). The tubes are placed 10° from upright, so that the balls roll along the wall of the tubes. The tubes are rotated 180° clockwise and anti-clockwise during the measurement. The tubes are rotated as soon as the balls reach the bottom of the tubes, which is approximately 20 s. When the samples become unstable, the balls are stopped by coagulated particles. The time needed to reach coagulation is recorded as the HCT. The reported heating times do not include the heating-up period, which is approximately 4 min. Hence, the HCT is only determined once the temperature reaches its constant value.

1.3. Oil Bath

We used an oil bath to determine heat-induced changes, because larger sample volumes could be heated than in the Klarograph. The samples were inserted in heat-resistant glass tubes of 15 ml (at least three tubes per sample) and heated for 15, 35, and 55 min in the oil bath. Similar samples were pooled after heating to obtain sufficient volume for analyses. The oil bath was set at 126° C. The time of heating did not include the heating-up of the samples, which was approximately 6 min. The samples were cooled in cold water until they reached ambient temperature, which was within 30 min, before analyses were done.

1.4. pH

The pH was measured at ambient temperature with an Inlab® Expert Pro pH meter (Mettler Toledo, Greifensee, Switzerland), which is part of the calcium-ion measuring device. The pH meter was calibrated with stock solutions of pH 4.0 and pH 7.0. The pH value was read after gently stirring for 5 min.

1.5. Calcium-Ion Activity

The calcium-ion activity was measured with a Mettler Toledo Seven Multi™ (with an Inlab® Expert Pro pH-meter) calcium measuring device (Mettler Toledo, Greifensee, Switzerland) using an Orion 9300BH electrode and an Orion 900100 reference electrode. Calibration of the electrodes, sample measurements, and calculations of the calcium-ion activities were performed as described in De Kort, E. J. P., Minor, M., Snoeren, T. H. M., van Hooijdonk, A. C. M., & van der Linden, E. (2009). Journal of Dairy Science and Technology, 89, 283-299.

16. Turbidity

The turbidity was measured with a spectrophotometer (4053 Kinetics, LKB 0, Midland, Canada). Plastic cuvettes with a path length of 1 cm were used. Measurements were carried out at ambient temperature using a wavelength of 700 nm. Samples were measured for their turbidity by diluting the samples to 10% of their initial dry matter in demineralized water so as to be within the detection limits of the spectrophotometer.

1.7. Viscosity

Samples were analyzed with a MCR 300 rheometer (Anton Paar Physica, Graz, Austria) using a cup (CC27 cylinder) and bob geometry. The viscosity was measured at shear rates of $1\ s^{-1}$ to $1000\ s^{-1}$. In this paper viscosity results at a shear rate of $50\ s^{-1}$ are given. Most of the samples behaved very similarly to Newtonian liquids.

1.8. Zeta Potential

The zeta potential was measured with the Zetasizer Nano Z (Malvern Instruments, Worcestershire, England) by using disposable folded capillary Zetasizer Nano cells of 1.5 ml (DTS1060, Malvern Instruments). Measurement of negative charges is based on the electrophoretic mobility in the samples. The zeta potential is calculated with the Smoluchowski approximation. Prior to analysis, samples were diluted to 1% of their initial dry matter in demineralized water and subsequently filtered through disposable Nalgene® Syringe celluloseacetate filters with a pore size of 0.8 µm (Nalgene Nunc International Corporation, Rochester, USA). Analyses were performed in duplicate at a cell temperature of 25° C. and voltage of 100 V.

2. RESULTS

In the first part the HCT results obtained with the Klarograph and the differences in calcium-ion activity, viscosity, turbidity, and zeta potential of the samples before heating are described. In the second part the heat-induced changes that were measured after heating the samples for various time periods in the oil bath are described.

2.1. Heat Coagulation Time

The HCT of the MCI solution with and without phosphates or citrate was measured at pH 6.7, 7.0, and 7.3 with the Klarograph for maximally 90 min. Calcium-ion activity, viscosity, turbidity, and zeta potential analyses were performed before heating to obtain information about changes in the concentration of free calcium ions, integrity of the micellar structure, and charge distribution on the micellar surface after addition of calcium chelators. Overviews of the results are shown for pH 6.7 in FIG. 1, pH 7.0 in FIG. 2, and pH 7.3 in FIG. 3. The HCT markedly increased upon addition of the calcium chelators, an effect which was most pronounced at pH 6.7. The differences in HCT were investigated in relation to the initial calcium-ion activity, viscosity, turbidity, and zeta potential of the samples. We can divide the results into four groups: 1) reference samples; 2) Na$_2$UMP; 3) Na$_2$HPO$_4$, TSC, and SP; 4) SHMP.

2.1.1. Reference Samples

The HCT of the reference samples (without chelators) increased with increasing pH: 2 min at pH 6.7, 40 min at pH 7.0, and 55 min at pH 7.3. This monotonic increase in HCT is in agreement with the HCT as function of pH for whey-protein-free casein micelle dispersions. The increase in HCT of the reference samples is due to the higher initial pH and concomitant lower calcium-ion activity. Besides these effects, the net negative charge of the casein micelles increases at higher pH. This induces more electrostatic repulsion between the negatively charged caseins, which gave an increase in heat stability. However, the changes in net negative charge were too small to detect with the zetasizer.

2.1.2. Addition of Na$_2$UMP

Na$_2$UMP is very effective in increasing the heat stability of the MCI solution at all three pH values (FIGS. 1 to 3). At higher pH a lower concentration of Na$_2$UMP was needed to give the MCI solution a HCT of more than 90 min. Na$_2$UMP reduced the concentration of free calcium ions by approximately 40% at pH 6.7 and 7.0, which greatly reduced protein aggregation. It is probable that below a calcium-ion activity of ~2 mmol·L$^{-1}$, enough free calcium ions were bound to give a strong increase in HCT. The viscosity, turbidity, and zeta potential of the solutions remained constant at all pH values. Therefore, it is most likely that the decrease in calcium-ion activity was the main driver for the increase in HCT in Na$_2$UMP samples.

2.1.3. Addition of Na$_2$HPO$_4$, TSC, and SP

Addition of Na$_2$HPO$_4$, TSC, and SP induced large increases in HCT at pH 6.7 and 7.0 (FIGS. 1 and 2). The increase in HCT was less pronounced at pH 7.3 (FIG. 3), because the HCT was already high for the reference sample. Addition of Na$_2$HPO$_4$ resulted in HCTs of more than 90 min at pH 7.0 and 7.3, whereas slightly lower HCTs were obtained for TSC and SP at these pH values. The calcium-ion activities, viscosities, and zeta potentials measured for Na$_2$HPO$_4$, TSC, and SP samples were of the same order at all three pH values. At pH 6.7 the large increase in HCT is most likely due to the strong decrease in calcium-ion activity. At pH 7.0 and 7.3 the calcium-ion activities stayed below 1.5 mmol L$^{-1}$ and 1.0 mmol L$^{-1}$, respectively, and this was sufficiently low to give the samples a high HCT.

The slight differences in HCT that were measured for Na$_2$HPO$_4$, TSC, and SP might be related to their differences in turbidity before heating. The decrease in turbidity is due to dissociation of the casein micelles into smaller structures upon addition of calcium chelators. It was concluded that micellar dissociation most probably occurred in the order SP>TSC>Na$_2$HPO$_4$. Hence, the MCI solutions with Na$_2$HPO$_4$, TSC, and SP contain different concentrations of dissociated and intact casein micelles. A decreasing trend in heat stability was measured in the order SP>TSC>Na$_2$HPO$_4$ at pH 7.0 and 7.3, which suggests that the small micellar particles formed have a negative impact on the heat stability of the MCI solution. However, these small micellar particles are also present in sodium caseinate at high ionic strength, whereas sodium caseinate is known for its high heat stability. Nevertheless, it is known that the heat stability of sodium caseinate can be markedly reduced in the presence of ionic calcium, It is also known that the heat stability of sodium caseinate and CCP-free milk shows a greater reduction in the presence of heat-precipitated calcium phosphate than milk containing unaltered casein micelles. As our samples contained a high concentration of calcium (phosphate) it is likely that the smaller micellar particles formed upon chelator addition were more susceptible to calcium-induced protein-aggregation than intact micelles. As a result, lower heat stabilities were measured for SP and TSC than for Na$_2$HPO$_4$. It is also known that the decrease in heat stability of recombined concentrated milk containing Na$_2$HPO$_4$, TSC, or EDTA was more pronounced when more casein micelles were dissociated.

The HCT of both Na$_2$HPO$_4$ and Na$_2$UMP samples increased to approximately 90 min or more at pH 7.0 and 7.3, whereas the HCT of Na$_2$HPO$_4$ samples was considerably lower than for Na$_2$UMP samples at pH 6.7. Addition of 15 mEq L$^{-1}$ Na$_2$HPO$_4$ or Na$_2$UMP at pH 6.7 reduced the concentration of free calcium ions by approximately 55% and 25%, respectively, because Na$_2$HPO$_4$ has a stronger calcium-binding capacity than Na$_2$UMP. The decrease in free calcium ions was sufficient to obtain a HCT of more than 70 min for Na$_2$HPO$_4$, but for Na$_2$UMP a HCT of just 40 min was measured. The HCT increased more for Na$_2$UMP than for Na$_2$HPO$_4$ at higher chelator concentrations at pH 6.7. The calcium-ion activity in both samples was sufficiently low to increase the HCT. However, in Na$_2$HPO$_4$ samples the amount of CCP in the micelles increased, most likely because of precipitation of calcium phosphate complexes in the casein micelle, whereas in Na$_2$UMP samples the amount of CCP was negligibly affected. This increase in amount of CCP decreased the HCT of Na$_2$HPO$_4$ samples.

2.1.4. Addition of SHMP

The lowest HCTs were measured for addition of SHMP at pH 6.7 and 7.0 in comparison to the other calcium chelators. The SHMP samples became very viscous with increasing SHMP concentration, which made it difficult to determine coagulation, because the glass balls could not freely move in the Klarograph tubes. The high viscosities are due to the cross-links formed between the caseins by SHMP. Samples were gelled upon addition of more than 45 mEq L$^{-1}$ SHMP at all three pH values. Addition of ≥45 mEq L$^{-1}$ SHMP at pH 7.3 caused a sharp decrease in the HCT, which is probably due to the high initial viscosity. A strong decrease in zeta potential was also observed for these samples. The net negative charge of the casein micelles and depletion of CCP from the casein micelles could have reached a critical value, at which κ-casein could not be retained on the micellar surface and the micellar structures could not be kept intact during heating. Moreover, the turbidity results indicate that most of the casein micelles were already dissociated at >45 mEq L$^{-1}$ SHMP before heating. This may have caused a strong increase in coagulation for the SHMP samples, because the small micellar particles formed upon calcium chelator addition are more susceptible to protein-aggregation.

It is remarkable that approximately −6 to −10 mV more negative zeta potentials were measured for SHMP than for SP samples at all three pH values (see zeta potentials in FIGS. 1 to 3). An equal amount of charges was added to the solutions and both polyphosphates can bind to the casein micelles, increasing the net negative charge of the casein micelles. It was hypothesized that SHMP interacts with the caseins and calcium ions (i.e. forms cross-links), whereas SP initially interacts more strongly with the calcium ions than with the casein micelles. This is related to the pK$_a$, form, and charge distribution of the SHMP and SP molecules. SHMP has more homogeneously distributed charges around its molecule, whereas SP has twelve negative charges, clustered in pairs, around its molecule. This might have resulted in more negatively charged casein micelles in SHMP samples.

2.2 Heat-Induced Changes

Samples with 0, 15, and 60 mEq L$^{-1}$ phosphate or citrate were selected and heated for 15, 35, and 55 min in the oil bath to determine heat-induced changes. A concentration of 15 mEq L$^{-1}$ was selected, because the largest increase in HCT was measured between 0 and 15 mEq L$^{-1}$. The samples were analyzed for their pH, calcium-ion activity, turbidity, viscosity, and zeta potential after heating. The results can be divided in three groups: 1) reference samples; 2) Na$_2$UMP, Na$_2$HPO$_4$, TSC, and SP; 3) SHMP. This classification is based on the fact that comparable heat-induced changes were measured for Na$_2$UMP and Na$_2$HPO$_4$, TSC, and SP, although they showed different HCTs (FIGS. 1 to 3).

2.2.1. Reference Samples

The results of the reference samples, without chelator addition, are summarized in Table 1.

TABLE 1

Reference samples at pH 6.7, 7.0, and 7.3 heated in the oil bath for 0-55 min

| pH | Time (min) | Measured pH (—) | Calcium-ion activity (mmol L$^{-1}$) | Turbidity (—) | Viscosity (mPa s) | Zeta potential (mV) |
|---|---|---|---|---|---|---|
| 6.7 | 0 | 6.70 | 2.57 | 2.65 | 3.31 | −22.83 |
|  | 15 | 6.48 | 1.39 | 3.00 | coagulated | −27.85 |
|  | 35 | 6.46 | 1.44 | 3.00 | coagulated | −28.00 |
|  | 55 | 6.41 | 1.34 | 3.00 | coagulated | −26.60 |
| 7.0 | 0 | 7.00 | 1.47 | 2.51 | 4.18 | −23.25 |
|  | 15 | 6.71 | 0.91 | 2.93 | 3.04 | −22.30 |
|  | 35 | 6.71 | 0.99 | 2.95 | 3.14 | −22.95 |
|  | 55 | 6.58 | 0.97 | 2.98 | 3.72 | −21.73 |
| 7.3 | 0 | 7.30 | 0.71 | 2.30 | 4.45 | −21.55 |
|  | 15 | 6.94 | 0.80 | 2.53 | 3.12 | −19.56 |
|  | 35 | 6.85 | 0.80 | 2.50 | 3.01 | −22.63 |
|  | 55 | 6.67 | 0.84 | 2.60 | 3.10 | −24.04 |

The pH decreased by 0.3 to 0.6 units during heating and it decreased more in the samples with higher initial pH. This decrease in pH is also observed for skim milk. The pH decrease is attributed to calcium phosphate precipitation rather than formation of formic acid, because MCI contains a negligible amount of lactose. The initial calcium-ion activity was higher than ~2 mmol·L$^{-1}$ at pH 6.7, which likely caused coagulation within 15 min of heating and a pH decrease to 6.5. The strong decrease in calcium-ion activity at pH 6.7 during heating also indicates calcium phosphate precipitation and protein aggregation, which resulted in a more negative zeta potential, increase in turbidity, and coagulation of the sample. These heat-induced changes were also observed at pH 7.0 and 7.3.

2.2.2. Addition of Na$_2$UMP, Na$_2$HPO$_4$, TSC, or SP

The pH decrease after heating for 55 min in the oil bath for 15 and 60 mEq L$^{-1}$ Na$_2$UMP, Na$_2$HPO$_4$, TSC, and SP samples at pH 6.7, 7.0, and 7.3 was comparable to the pH decrease that was measured for the reference samples (see Table 1). None of these samples showed visible coagulation after heating for 55 min in the oil bath. The calcium-ion activities of these samples remained constant or slightly decreased. The calcium-ion activities before heating were already sufficiently low because of the calcium-binding capacity of the chelators and the stronger calcium phosphate binding in the micelles with increasing pH (FIGS. 1 to 3). Small changes could be detected for the zeta potential of these samples. The turbidity increased and viscosity decreased in the samples during heating, because calcium phosphate precipitation and decomposition of the caseins occurred.

In FIG. 4 it is shown that the turbidity of the MCI solution with 60 mEq L$^{-1}$ SP at pH 7.3 only slightly increased during heating. This sample behaved remarkably differently than the samples with 0 or 60 mEq L$^{-1}$ Na$_2$HPO$_4$ or TSC. SP probably binds the calcium ions so strongly (also at lower pH) that only a low concentration of calcium ions is available for heat-induced calcium phosphate precipitation or calcium-induced protein-aggregation. Moreover, the electrostatic repulsion between the micelles is stronger at lower calcium-ion activity, which reduces protein-aggregation. The strongly charged anionic SP molecules might also bind to the positively charged amino acid residues, increasing the electrostatic repulsion between the casein micelles as well. This resulted in a HCT of more than 90 min for addition of 60 mEq L$^{-1}$ SP at pH 7.3 (FIG. 3). Only a slight decrease in viscosity and increase in zeta potential was measured for this SP sample during heating (FIG. 4), because the strong repulsion between the caseins and strong calcium binding capacity of SP was probably maintained during heating.

FIG. 4 shows that the viscosity of the 60 mEq L$^{-1}$ Na$_2$HPO$_4$ or TSC samples at pH 7.3 strongly decreased during heating, to values that were slightly higher than the reference samples. The decrease in viscosity is related to the changes that occur in the micelles during heating. It is known for milk that during heating the viscosity decreases because of dissociation of the micelles (i.e. solubilization of casein and CCP and release of κ-casein). These heat-induced changes make the dissociated casein micelles more susceptible to coagulation. Hence, with the onset of coagulation, the viscosity strongly increases. In the Na$_2$UMP, Na$_2$HPO$_4$, TSC, and SP samples this strong increase in viscosity was not measured, because the samples did not coagulate in the oil bath.

2.2.3. Addition of SHMP

SHMP gave a more pronounced decrease in pH during heating than the reference samples and the other calcium chelators at all three pH values: a pH decrease of 0.7-0.9 (Table 2) versus 0.3-0.6 (Table 1). This caused an increase in the concentration of free calcium ions, which made the samples more susceptible to calcium-induced protein aggregation. As a result, coagulation was measured after heating 55 min in the oil bath upon addition of 15 or 60 mEq L$^{-1}$ SHMP at pH 6.7. These low heat stabilities are in agreement with the low HCTs that were measured for these samples (FIG. 1). In a previous study (De Kort, E. J. P., Minor, M., Snoeren, T. H. M., van Hooijdonk, A. C. M., & van der Linden, E. (2009). Journal of Dairy Science and Technology, 89, 283-299), a strong decrease in pH for SHMP in a calcium chloride solution upon heating was observed. SHMP hydrolyzes into sodium trimetaphosphate and sodium orthophosphate in acidic conditions and this hydrolysis probably occurred in the MCI solutions during heating as well. This induced, besides the strong pH decrease, the release of calcium ions, which can cause calcium-induced protein aggregation. The calcium-ion activity was lower at higher pH and upon addition of 60 mEq L$^{-1}$ SHMP, as more calcium ions were part of the CCP complexes or bound to SHMP, respectively. Moreover, less SHMP will be hydrolyzed at higher pH.

The strong decrease in viscosity and increase in zeta potential (e.g. from −33.10 to −21.15 mV at pH 6.7 for 60 mEq L$^{-1}$) in the SHMP samples at all three pH values indicate that the cross-links formed before heating between the caseins and SHMP were broken during heating. As an increase in calcium-ion activity was measured during heating, it is likely that calcium ions were involved in the cross-links as well. The increase in the concentration of free calcium ions during heating most probably initiated calcium-induced protein-aggregation. The strong increase in zeta potential may be caused by the release of SHMP from the micelles or by release of κ-casein from the casein micelles. κ-Casein depletion is more pronounced at higher pH, which reduced the net negative charge of the casein micelles and increased the sensitivity to protein-aggregation. As a result, a strong decrease in HCT was measured upon addition of ≥45 mEq L$^{-1}$ SHMP at pH 7.3 (FIG. 3). The turbidity also strongly increased during heating in all SHMP samples, which is attributed to calcium-induced protein-aggregation. Overall, the MCI solutions with SHMP are more susceptible to heat coagulation than those with the other calcium chelators because of the strong decrease in pH and increase in calcium-ion activity during heating.

TABLE 2

SHMP samples at pH 6.7, 7.0, and 7.3 heated in the oil bath for 0-55 min.

| | | 15 mEq L$^{-1}$ SHMP | | | | | 60 mEq L$^{-1}$ SHMP | | | | |
|---|---|---|---|---|---|---|---|---|---|---|---|
| pH | Time (min) | Measured pH (—) | Calcium-ion activity (mmol L$^{-1}$) | Turbidity (—) | Viscosity (mPa s) | Zeta potential (mV) | Measured pH (—) | Calcium-ion activity (mmol L$^{-1}$) | Turbidity (—) | Viscosity (mPa s) | Zeta potential (mV) |
| 6.7 | 0 | 6.70 | 1.13 | 2.08 | 6.04 | −25.85 | 6.70 | 0.30 | 0.11 | 144 | −33.10 |
| | 15 | 6.21 | 1.14 | 2.91 | 5.66 | −24.78 | 6.06 | 0.40 | 2.79 | 5.53 | −22.93 |
| | 35 | 6.24 | 1.37 | 2.56 | coagulated | −24.13 | 5.94 | 0.49 | 2.86 | 6.53 | −24.40 |
| | 55 | 6.04 | 1.92 | 2.63 | coagulated | −22.10 | 5.85 | 0.54 | 2.52 | coagulated | −21.15 |
| 7.0 | 0 | 7.00 | 0.72 | 1.79 | 14.0 | −27.40 | 7.00 | 0.21 | 0.13 | 331 | −37.93 |
| | 15 | 6.50 | 0.61 | 1.76 | 5.04 | −27.57 | 6.29 | 0.30 | 2.07 | 5.54 | −27.87 |
| | 35 | 6.36 | 0.74 | 2.13 | 3.26 | −24.52 | 6.17 | 0.26 | 2.58 | 4.30 | −28.57 |
| | 55 | 6.27 | 0.42 | 2.66 | 3.77 | −25.13 | 6.10 | 0.31 | 2.73 | coagulated | −23.25 |
| 7.3 | 0 | 7.30 | 0.41 | 0.75 | 115 | −31.33 | 7.30 | 0.14 | 0.09 | 593 | −43.00 |
| | 15 | 6.76 | 0.56 | 2.62 | 4.08 | −26.58 | 6.78 | 0.54 | 1.86 | 11.1 | −27.60 |
| | 35 | 6.74 | 0.30 | 1.99 | 3.89 | −27.40 | 6.65 | 0.28 | 2.44 | 10.8 | −26.53 |
| | 55 | 6.60 | 0.23 | 2.36 | 4.27 | −24.95 | 6.57 | 0.15 | 2.49 | 9.39 | −24.53 |

3. DISCUSSION

Without being bound by theory, this research has shown that the influence of the various calcium chelators on the heat stability of the MCI solution is determined by the initial calcium-ion activity, the amount of CCP in the casein micelle, and the extent of dissociation of the casein micelle.

A low calcium-ion activity was the most important parameter to effectively increase the HCT of the MCI solution. The weak calcium chelator Na$_2$UMP is a very effective heat stabilizer, because it decreased the calcium-ion activity sufficiently without affecting the micellar structure. As a result, the highest HCTs were measured for Na$_2$UMP at all three pH values. An effect was also obtained with increasing pH: the calcium-ion activity decreased, the protein charge increased and, consequently, the HCT increased. Na$_2$HPO$_4$, TSC, and SP also increased the HCT of the MCI solution by decreasing the calcium-ion activity to comparable levels, but their effect on the HCT was smaller than for Na$_2$UMP. This is probably because these chelators affected the amount of CCP in the casein micelle and integrity of the micellar structure as well. Reduction of the level of CCP is known to increase the heat stability of milk below pH 7.0. However, when a critical level of CCP is removed from the micelles, it is known they start to dissociate, which decreases heat stability. Na$_2$HPO$_4$ precipitates with calcium on the micelle and thereby the amount of CCP in the micelle increases. This implies that a lower HCT should be measured for Na$_2$HPO$_4$ than for TSC or SP. However, a decrease in heat stability occurred in the order SP>TSC>Na$_2$HPO$_4$. It was concluded that these chelators most probably dissociate the micelles in the order SP>TSC>Na$_2$HPO$_4$. Therefore, it is likely that slight differences in heat stability for these samples are mainly attributable to the extent of micellar dissociation and not to the amount of CCP present in the casein micelles. The small micellar particles formed upon micelle dissociation in the MCI solutions seem more susceptible to calcium-induced protein-aggregation than intact casein micelles.

Heat-induced changes that occurred in the reference, Na$_2$UMP, Na$_2$HPO$_4$, TSC, and SP samples during heating were of the same order. This implies that the differences in HCT of these samples were mainly determined by the state of the MCI solutions before heating.

Contrary to the other calcium chelators, the heat-induced changes that occurred in the SHMP samples did play an important role for their heat stability. Of course the calcium-ion activity and state of the micellar structure before heating were also important for the heat stability of these SHMP samples. However, the results indicate that the strong decrease in pH, increase in calcium-ion activity, and breakdown of SHMP cross-links between the caseins during heating were mainly responsible for the strong decrease in the HCT of SHMP samples.

4. CONCLUSIONS

The heat stability of a MCI solution can be improved by addition of calcium chelators. Na$_2$UMP is the most effective heat stabilizer, as it binds sufficient free calcium ions to reduce protein aggregation without affecting the integrity of the micellar structure. The HCT of the MCI solutions with Na$_2$HPO$_4$, TSC, and SP increased to comparable levels compared to one another, but the increase in HCT was much smaller than for Na$_2$UMP. The slight differences in HCT that were measured for these samples other than Na$_2$UMP were due to the extent to which the casein micelles were dissociated. This made the MCI solutions more susceptible to coagulation. SHMP was the least effective heat stabilizer. SHMP cross-linked the caseins, but these cross-links were broken during heating. This decreased the pH and increased the calcium-ion activity during heating, which reduced the heat stability of the SHMP samples.

In conclusion, calcium chelators increase the heat stability of the MCI solution to different extents and these differences are attributable to the calcium-ion activity and state of the micellar structure before heating. Optimization of heat stability of dairy systems is complex and therefore selection of the type and concentration of calcium chelator requires careful investigation. Surprisingly, pronounced effects on heat stability are observed with nucleotides.

The invention claimed is:

1. A method for improving the heat stability of an aqueous micellar casein composition having a pH of about 6 to 8 and comprising (a) 11 to 20 g of protein per 100 ml of the composition, in which at least 80 wt % of the protein comprises micellar casein, and wherein 0-15 weight % of the protein present in the nutritional composition comprises whey, the method comprising adding (b) 45 to 120 mEq.L$^{-1}$ of one or more nucleotides to the composition, wherein the composition has a heat coagulation time (HCT) value which is at least 10% higher than the HCT value for a reference composition not including the one or more nucleotides.

2. The method according to claim 1, wherein the nucleotides are selected from the group consisting of uridine monophosphate (UMP), cytidine monophosphate (CMP), thymidine monophosphate (TMP), guanosine monophosphate (GMP), adenosine monophosphate (AMP), and inosine monophosphate (IMP).

3. The method according to claim 2, wherein the monophosphate is a sodium phosphate, a potassium phosphate, or a mixture thereof.

4. The method according to claim 3, wherein the nucleotide monophosphate is disodium uridine monophosphate or disodium cytidine monophosphate.

5. The method according to claim 1, wherein 45 to 100 $mEq.L^{-1}$ of the one or more nucleotides is added to the composition.

6. The method according to claim 5, wherein 45 to 60 $mEq.L^{-1}$ of the one or more nucleotides is added to the composition.

7. The method according to claim 1, wherein at least 80 wt % of the proteins of the composition is micellar casein proteins of the composition are micellar casein.

8. A liquid nutritional composition having a pH of about 6 to 8 and comprising:
(a) 11 to 20 g of protein per 100 ml of the composition, in which at least 80 wt % of the protein comprises micellar casein, and wherein 0-15 weight % of the protein present in the nutritional composition comprises whey, and
(b) 45 to 120 $mEq.L^{-1}$ of one or more nucleotides,
wherein the composition has a heat coagulation time (HCT) value which is at least 10% higher than the HCT value for a reference composition not including the one or more nucleotides.

9. The composition according to claim 8, wherein the nucleotides are selected from the group consisting of uridine monophosphate (UMP), cytidine monophosphate (CMP), thymidine monophosphate (TMP), guanosine monophosphate (GMP), adenosine monophosphate (AMP), and inosine monophosphate (IMP).

10. The composition according to claim 9, wherein the monophosphate is a sodium phosphate, a potassium phosphate, or a mixture thereof.

11. The composition according to claim 10, wherein the nucleotide monophosphate is disodium uridine monophosphate or disodium cytidine monophosphate.

12. The composition according to claim 8, wherein the composition comprises 45 to 100 $mEq.L^{-1}$ of the one or more nucleotides.

13. The composition according to claim 12, wherein the composition comprises 45 to 60 $mEq.L^{-1}$ of the one or more nucleotides.

14. The composition according to claim 8, wherein at least 90 wt % of the protein comprises micellar casein.

15. The composition according to claim 8, further comprising one or more of fat, digestible and non-digestible carbohydrates.

16. The composition according to claim 8, wherein the composition is pasteurized or sterilized.

17. The composition according to claim 8, wherein the composition is subjected to a temperature of at least 60° C. for at least a time t (in seconds)=(500/(T−59))−4, in which temperature T is expressed in ° C. and t is at least 0.1 sec.

18. The composition according to claim 8, wherein the composition has a sterilizing value or Fzero value of at least 2.8 minutes.

19. A process for the heat treatment of an aqueous micellar casein composition having a pH of about 6 to 8 and comprising (a) 11 to 20 g of protein per 100 ml of the composition, in which at least 80 wt % of the protein comprises micellar casein, and wherein 0-15 weight % of the total protein present in the composition comprises whey, the process comprising adding (b) 45 to 120 $mEq.L^{-1}$ of one or more nucleotides to the composition prior to the heat treatment, wherein the composition has a heat coagulation time (HCT) value which is at least 10% higher than the HCT value for a reference composition not including the one or more nucleotides.

20. The process according to claim 19, wherein 45 to 100 $mEq.L^{-1}$ of the nucleotide(s) is added to the composition.

21. A method of providing nutrition to a person in need thereof, comprising administering to said person the nutritional composition according to claim 8, wherein the person is an elderly person, a person who is in a disease state, a person who is recovering from a disease state, a person who is malnourished, or a healthy person.

22. A liquid nutritional composition having a pH of about 6 to 8 and comprising:
(a) 11 to 20 g of protein per 100 ml of the composition, in which at least 80 wt % of the protein comprises micellar casein, and wherein 0-15 weight % of the protein present in the nutritional composition comprises whey, and
(b) 45 to 120 $mEq.L^{-1}$ of one or more nucleotides,
wherein the composition does not show coagulation after heating for 90 minutes in a Klarograph using a 126° C. oil bath.

23. The liquid nutritional composition according to claim 8, wherein the composition has an energy density of at least 1.0 kcal/ml.

* * * * *